US007783358B2

(12) United States Patent
Aldrich et al.

(10) Patent No.: US 7,783,358 B2
(45) Date of Patent: *Aug. 24, 2010

(54) METHODS AND APPARATUS FOR TREATMENT OF OBESITY WITH AN ULTRASOUND DEVICE MOVABLE IN TWO OR THREE AXES

(75) Inventors: William N. Aldrich, Napa, CA (US); David Miller, Palo Alto, CA (US)

(73) Assignee: Endovx, Inc., Napa, CA (US)

( * ) Notice: Subject to any disclaimer, the term of this patent is extended or adjusted under 35 U.S.C. 154(b) by 1270 days.

This patent is subject to a terminal disclaimer.

(21) Appl. No.: 11/067,063

(22) Filed: Feb. 24, 2005

(65) Prior Publication Data

US 2005/0203501 A1 Sep. 15, 2005

Related U.S. Application Data

(63) Continuation-in-part of application No. 10/389,236, filed on Mar. 14, 2003, now Pat. No. 7,684,865.

(51) Int. Cl.
*A61N 1/08* (2006.01)
(52) U.S. Cl. ........................................ 607/40; 607/112
(58) Field of Classification Search .................. 607/40, 607/112; 600/554, 561
See application file for complete search history.

(56) References Cited

U.S. PATENT DOCUMENTS

| 5,188,104 | A | 2/1993 | Wernicke et al. |
| 5,263,480 | A | 11/1993 | Wernicke et al. |
| 5,720,287 | A | 2/1998 | Chapelon et al. |
| 5,807,285 | A | 9/1998 | Vaitekunas et al. |
| 6,197,022 | B1 | 3/2001 | Baker |
| 6,371,903 | B1 | 4/2002 | Blanc et al. |
| 6,405,732 | B1 | 6/2002 | Edwards et al. |
| 6,669,655 | B1 | 12/2003 | Acker et al. |

(Continued)

FOREIGN PATENT DOCUMENTS

WO  WO 00/69376  11/2000

(Continued)

OTHER PUBLICATIONS

Lele, P.P., Effects of Focused Ultrasonic Radiation on Peripheral Nerve, with Observations on Local Heating, Experimental Neurology, vol. 8, pp. 47-83 (1963).

(Continued)

*Primary Examiner*—Carl H. Layno
*Assistant Examiner*—Tammie K. Heller
(74) *Attorney, Agent, or Firm*—Orrick, Herrington & Sutcliffe LLP

(57) ABSTRACT

Method and apparatus for treating obesity by an energy delivery device, such as a high focus ultrasound transducer, mounted for movement along two or three axes relative to the esophagus to deliver transesophageal energy to interrupt the function of vagal nerves. Preferably, movement along a longitudinal axis of the esophagus changes the site to which the energy is directed and movement transversely along a radius of the esophagus focuses the energy on a vagal nerve. The third degree of freedom relative to the esophagus is to rotate the transducer about the longitudinal axis of the esophagus.

28 Claims, 14 Drawing Sheets

U.S. PATENT DOCUMENTS

| | | | |
|---|---|---|---|
| 2002/0068963 | A1 | 6/2002 | Maki et al. |
| 2002/0087192 | A1 | 7/2002 | Barrett et al. |
| 2002/0138075 | A1 | 9/2002 | Edwards et al. |
| 2003/0023287 | A1 | 1/2003 | Edwards et al. |
| 2004/0082859 | A1 | 4/2004 | Schaer |
| 2004/0267167 | A1 | 12/2004 | Podany et al. |

FOREIGN PATENT DOCUMENTS

| | | |
|---|---|---|
| WO | WO 01/22897 A1 | 4/2001 |
| WO | WO 2004/082763 A | 9/2004 |

OTHER PUBLICATIONS

Bell, P.R.F., The Long Term Effect of Vagotomy On The Maximal Acid Response to Histamine In Man, Univ. Dept. of Surgery, Royal Infirmary, Sheffield, England, vol. 46, No. 4, pp. 387-391.

Burge, H. et al., Method Of Testing For Complete Nerve Section During Vagotomy, British Medical Journal, Mar. 15, 1958, pp. 615-618.

Burge, H. et al., The Technique Of Bilateral Selective Vagotomy With The Electrical Stimulation Test, Brit. J. Surg., vol. 56, No. 6, Jun. 1969, pp. 452-460.

Date, Y. et al., The Role of the Gastric Afferent Vagal Nerve in Ghrelin-Induced Feeding and Growth Hormone Secretion in Rats, Gastroenterology 2002; 123: 1120-1128.

Date, Y. et al., Ghrelin Acts in the Central Nervous System to Stimulate Gastric Acid Secretion, Biochem. and Biophys. Res. Communications, 280, 904-907 (2001).

Goto, Y. et al., A New Intraoperative Test for Completeness of Vagotomy: The PCP-GABA (Beta-Parachiorophenol-Gamma-Aminobutyric Acid) Test, The American J. of Surgery, vol. 147, Jan. 1984, pp. 159-163.

Grassi, G. et al., Intraoperative Relation Of Gastic Secretion Acidity and Complete Vagotomy, Surgery, Gynecology & Obstetrics, vol. 134, Jan. 1972, pp. 35-38.

Hennessy, T.P.J. et al., An improved preoperative test of vagal section, Annals of the Royal College of Surgeons of England, vol. 61, 1979, pp. 474-476.

Kral, J.G. et al., Gastroplasty for Obesity: Long-Term Weight Loss Improved by Vagotomy, World J. Surg. 17, 75-79 (1993).

Kral, J. G., Surgical Treatment of Obesity, Medical Clinics of North America, vol. 73, No. 1, Jan. 1989.

Kral, J.G., Behavioral effects of vagotomy in humans, J. of Autonomic Nervous System, 9 (1983) 273-281.

Kral, J.G. et al., Truncal vagotomy in morbid obesity, Int'l J. of Obesity (1981) 5, 431-435.

Nagammapudur, S. et al., A Safe and Noninvasive Test for Vagal Integrity Revisited, Arch. Surg., vol. 137, Aug. 2002, pp. 954-957.

Ross, B. et al., The Insulin Test After Vagotomy, The Univ. Dept. Of Surgery, The Royal Infirmary, Sheffield, England, vol. 46, No. 4, pp. 379-386.

DEVICE WITH UNDEPLOYED BALLOONS

DEVICE WITH DEPLOYED BALLOONS

METHODS AND APPARATUS FOR TREATMENT OF OBESITY WITH AN ULTRASOUND DEVICE MOVABLE IN TWO OR THREE AXES

CROSS REFERENCE TO RELATED PATENT APPLICATIONS

This application is a continuation-in-part of U.S. patent application Ser. No. 10/389,236, titled "Methods and Apparatus for Treatment of Obesity," filed Mar. 14, 2003 now U.S. Pat. No. 7,684,865.

FIELD OF THE INVENTION

The field of the present invention is methods and devices for treating obesity, and more particularly, methods and devices for treating obesity by disrupting the vagal nerve.

BACKGROUND OF THE INVENTION

Obesity has become an ever-increasing health problem. While such voluntary weight reduction programs as dieting and exercise have been helpful for some, many obese persons have required surgery to address their obesity problem. Two such surgical procedures are vertical banded gastroplasty (VBG) and the Roux-en-Y gastric bypass procedure. Both such procedures are now well known, but they are invasive in nature and involve reducing the size of the stomach. While these procedures have demonstrated a reasonable level of efficacy, there is a need for an improvement in the treatment of obesity that would avoid invasive surgery and providing an effective treatment of obesity.

SUMMARY OF THE INVENTION

The invention is, in general, directed to the treatment of obesity by creating an interruption of the vagal nerve, preferably in the region of the esophagus, by minimally or non-invasive means. While the present invention is not to be tied to any particular theory of operation, it appears that a hunger signal is expressed by ghrelin, a peptide primarily produced in the stomach, and transmitted to the brain through the vagal nerve. The literature e.g., "The Role of the Gastric Afferent Vagal Nerve in Ghrelin-Induced Feeding and Growth Hormone Secretion in Rats," *Gastroenterology* 2002:123:1120-1128 (October 2002) by Yukari Date et al. and "Gastroplasty for Obesity: Long-term Weight Loss Improved by Vagotomy," *World Journal of Surgery*, Vol. 17, No. 1, January/February 1993, by Kral et al., supports this theory. The Date et al. article concluded that blockade of the gastric vagal afferent abolished ghrelin-induced feeding in rats and the Kral et al. article concluded that vagotomy combined with gastroplasty was more effective in controlling weight loss than gastroplasty alone. These articles are incorporated by reference herein.

More specifically, the preferred embodiment of the invention uses an ultrasound device that is movable along up to three axes. In particular, the preferred embodiment has an ultrasound device may be moved longitudinally along the axis of the esophagus to a further or closer distal position, transversely along the radius of the esophagus, and rotationally about the axis of the esophagus. These three degrees of freedom are relative to the esophagus. Because the ultrasound device is movable along the radial axis, the device is better able to focus its energy output on the vagal nerve in the region of the esophagus to interrupt the function of the vagal nerve, while avoiding injury to the esophagus. After an ablating or other nerve dysfunction causing device installed in the esophagus is properly positioned, it may be used to deliver ablating energy to one or more vagal nerve branches in a transesophageal manner. The anatomy of the vagal nerve complex varies somewhat from person to person, but, common to all is a structure comprising multiple vagal nerve branches located on the outer wall of the esophagus which run generally longitudinally along the esophagus wall. The preferred embodiment contemplates interrupting the function of one or more vagal nerve branches in a transesophageal manner by using various types of energy including radio frequency (RF) energy, high intensity ultrasound, high intensity focused ultrasound, and other types of energy as described in more detail below.

Typically, there are two main branches, or trunks, of the vagal nerve which are located approximately 180° from each other on the outer wall of the esophagus. Depending on patient needs, it may be sufficient to interrupt only a portion of the fibers in the nerve. In this regard, it is to be noted that, in general, myelinated vagal nerve fibers, i.e., fibers that have an outer coating, are efferent. In contrast, afferent vagal nerves are unmyelinated and have no outer covering. For some patients, it may be sufficient to interrupt the function of only the afferent vagal fibers. However, the invention can be used to disrupt the vagal nerve at other locations, such as at the diaphragm.

The objective is, of course, weight loss by the patient as a result of interruption of efferent gastric and afferent hormonal signals transmitted through the vagal nerve branches. Thus, the success of the procedure described herein will, to some extent, be patient-dependent and, in some patients, it may be necessary to interrupt both the afferent and efferent vagal fibers, both of which may be found in the posterior and anterior branches.

In practicing the present invention, the energy source may be installed in the esophagus through the throat, but nasogastric access through the nose and extracorporeal application are also contemplated. The energy may be delivered to the vagal nerve through the esophagus wall, e.g., when ultrasound is used, or by causing an energy delivery device, e.g., an electrode to be passed through the wall of the esophagus.

Still other energy sources can be used to interrupt the function of the vagal nerves including thermal, microwave, laser and cryogenic energy. Alternatively, the vagal nerve function can be interrupted by transesophageal delivery of a neurotoxin such as capsaicin, atropine, or botulinum toxin. Still further, mechanical means can be used to crush the vagal nerve, e.g., with a clip or pincer, or the vagal nerve can be cut transesophageally with an appropriate cutting instrument. In a preferred embodiment of the present invention, the vagal nerve will be interrupted in the vicinity of the zig-zag line, also known as the Z-line, which is generally located in the lower esophagus between the cardiac notch of the stomach and the diaphragm.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

DESCRIPTION OF THE DRAWINGS

The details of the invention, including fabrication, structure and operation, may be gleaned in part by study of the accompanying figures, in which like reference numerals refer to like segments. The figures are not to scale and the size of the features in relation to each other is not intended to limit the invention in any way.

DETAILED DESCRIPTION OF THE INVENTION

Before turning to the manner in which the present invention functions, it is believed that it will be useful to briefly review the anatomy of the stomach and the esophagus. The esophagus is a muscular tube that carries food from the throat to the stomach and which passes through the diaphragm. The top end of the esophagus is the narrowest part of the entire digestive system and is encircled by a sphincter (circular muscle) that is normally closed but can open to allow the passage of food. There is a similar sphincter at the point where the esophagus enters the stomach. The walls of the esophagus consist of strong muscle fibers arranged in bundles, some circular and others longitudinal. The inner lining of the esophagus consists of smooth squamous epithelium (flattened cells).

Figure 1:
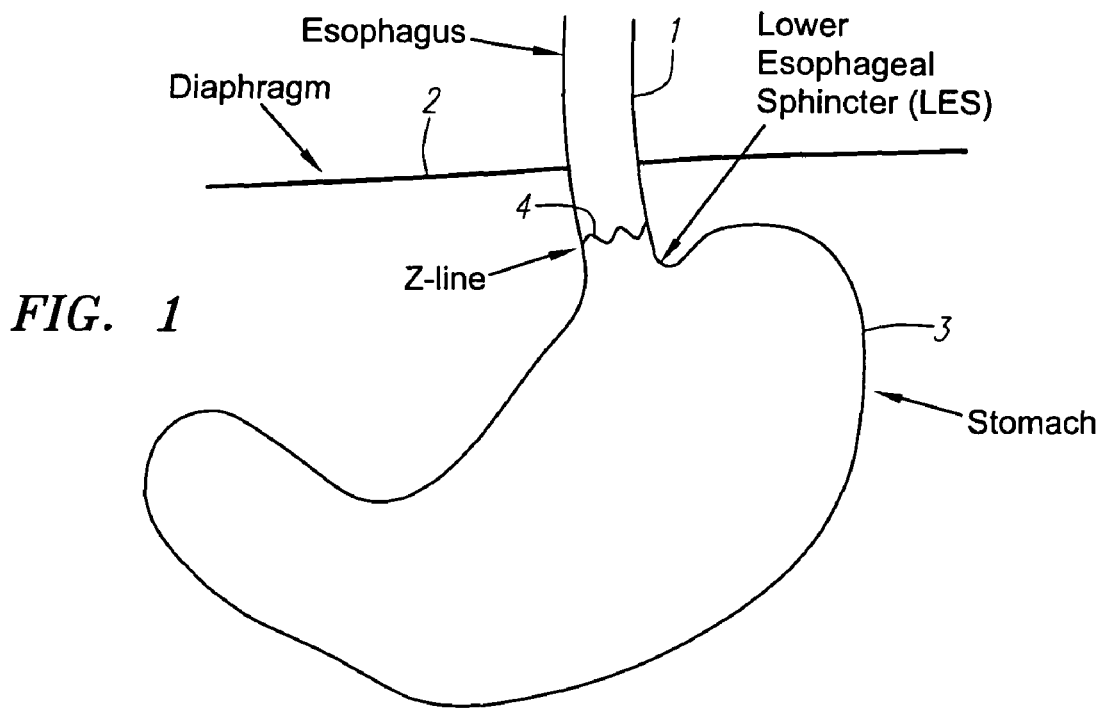
FIG. 1 is a diagrammatic illustration of the general anatomy of the stomach and esophagus.

As shown in FIG. 1, the esophagus 1 extends through the diaphragm 2 into the stomach 3. Vagal nerve branches extend from the stomach along the outer wall of the esophagus to the brain. At the lower end of the esophagus, the juncture of the esophageal and gastric mucosa forms a zig-zag line 4, usually referred to as the Z-line. In the area extending from the diaphragm to a point below the Z-line, there is a subhiatal fat ring which surrounds the outer wall of the esophagus. The vagal nerve branches run between the outer wall of the esophagus and the hiatal fat ring in this area. This anatomy is well understood by those skilled in the art and a more detailed description can readily be found in a standard work such as *Gray's Anatomy.*

Figure 2:
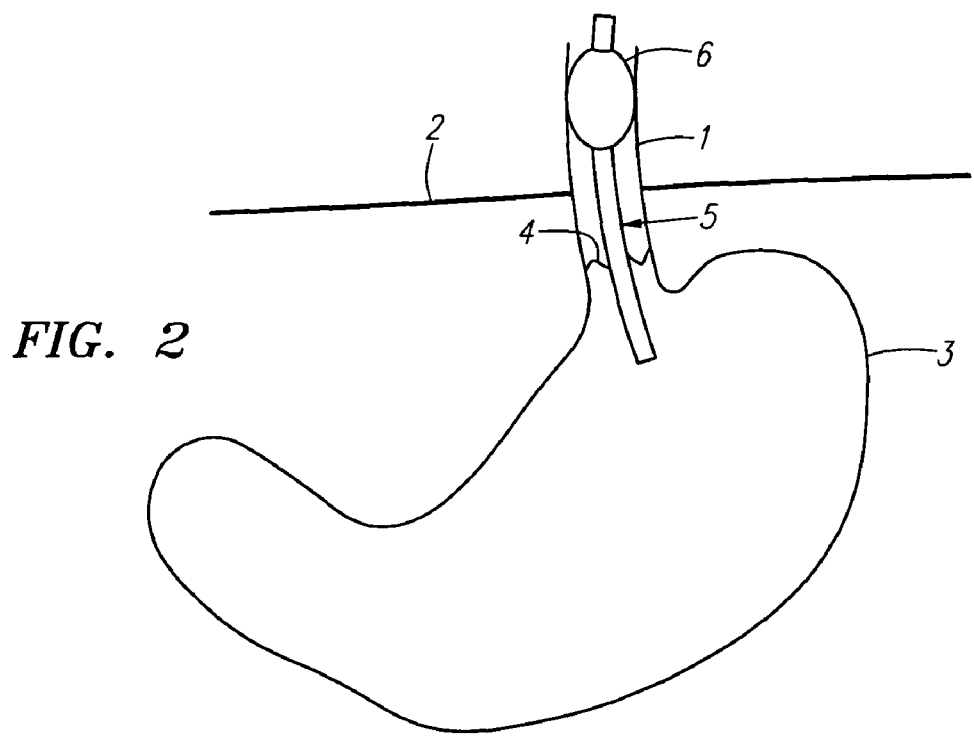
FIG. 2 illustrates positioning of an ablation device using a single balloon installed above the diaphragm.
Figure 3:
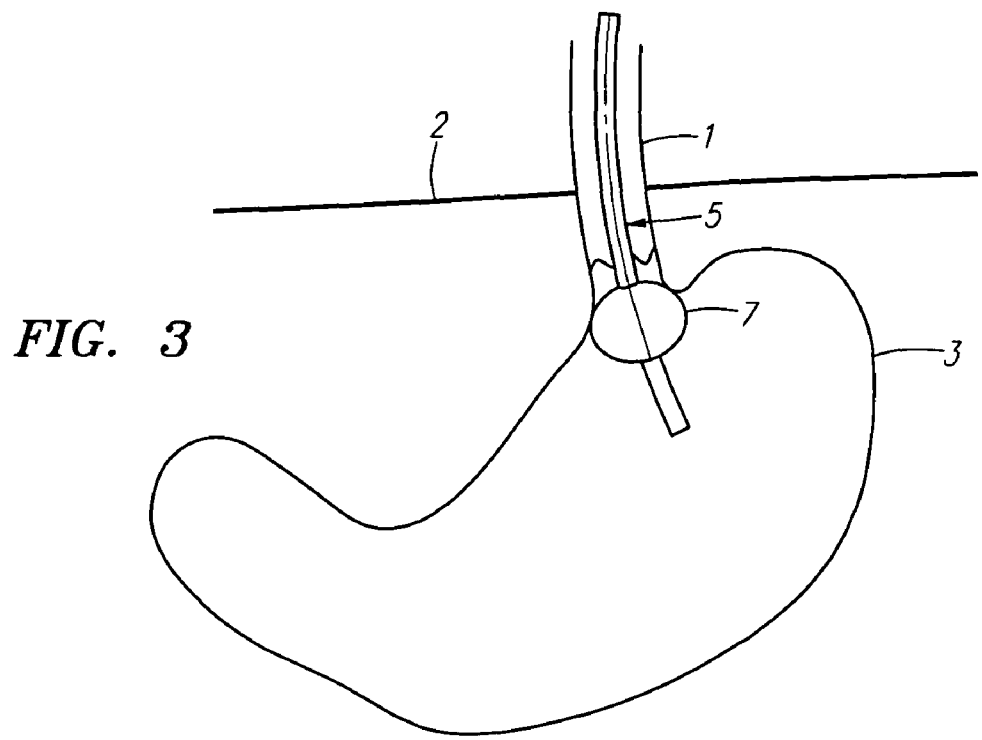
FIG. 3 illustrates positioning the ablation device using a balloon which is inflated in the stomach.
Figure 4:
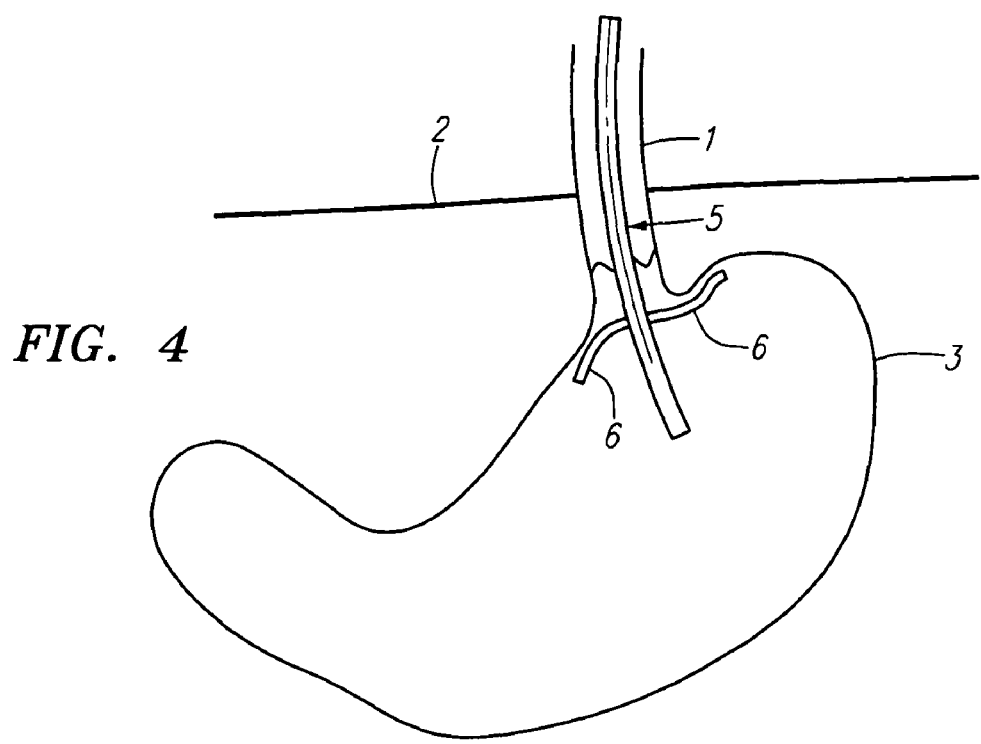
FIG. 4 illustrates a positioning device using radially extending feet.
Figure 5:
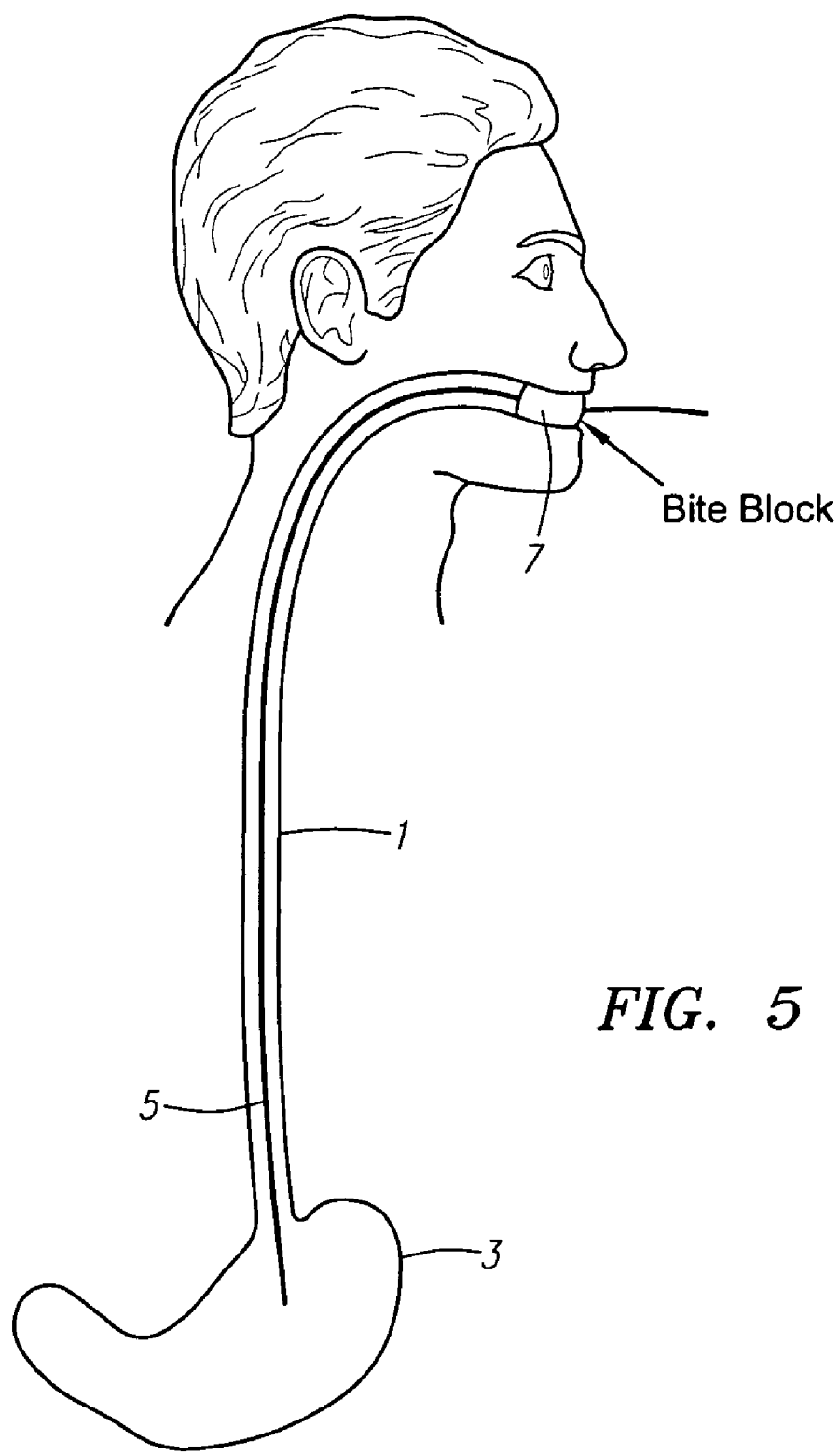
FIG. 5 illustrates a positioning device using a bite block.
Figure 6:
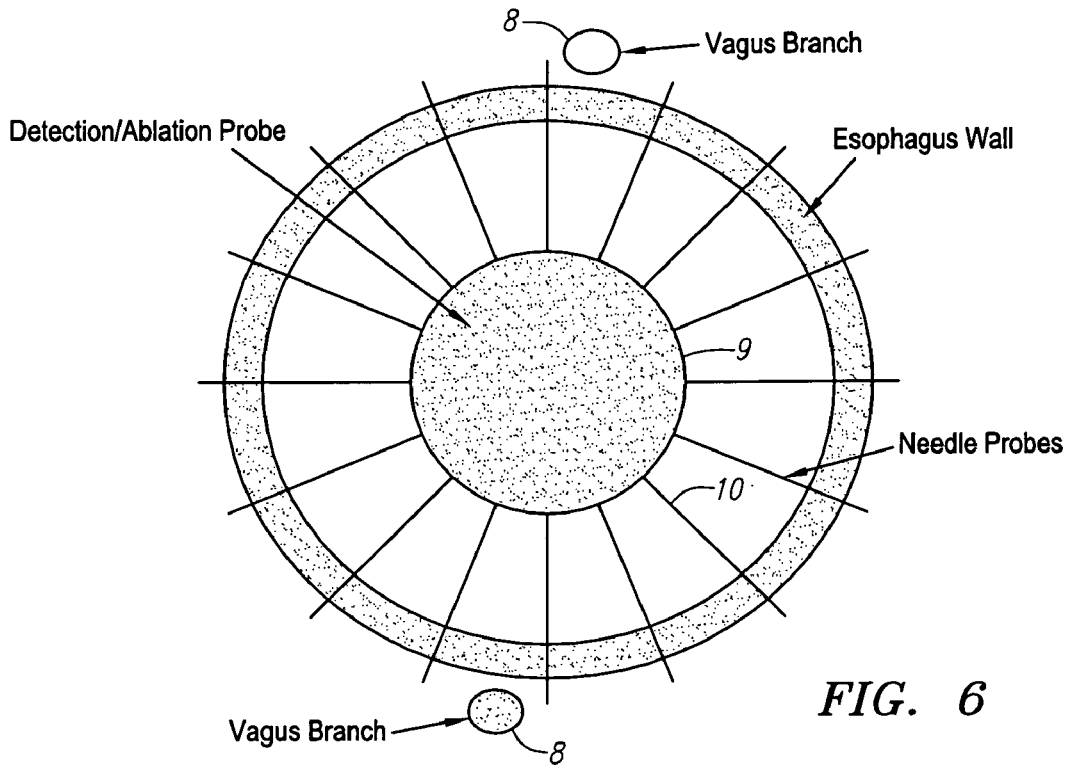
FIG. 6 is a diagrammatic illustrate of the use of needles or electrodes to detect and ablate around the circumference of the outer surface of the esophagus in a manner designed to interrupt all vagal nerve branches.

FIG. 2 illustrates in a diagrammatic manner an ablation device 5 which is held in place by balloon 6 which is inflated inside the upper portion of the esophagus. FIG. 3 illustrates positioning the ablation device 5 with balloon 7 which is inflated inside stomach 3. FIG. 4 illustrates positioning the ablation device 5 with feet 6 which pass through the esophagus folded against the ablation device 5 and then are extended inside stomach 3. FIG. 5 illustrates the use of a bite block 7 to position the ablation device 5 in stomach 3. FIG. 6 is a diagrammatic transverse cross section of the esophagus showing, in diagrammatic form, the esophagus wall 1, vagal nerve branches 8, a detection/ablation device 9 having needle probes 10. As shown, the needle probes 10 extend through the wall of the esophagus and can be used both to locate the vagus nerve and to ablate it. For detection purposes, the needle probes 10 are connected to an exterior control unit that detects and displays nerve activity in a manner well known to those skilled in the art. Once a vagal nerve is detected by a needle probe by sensing the activity of the nerve upon contact, the adjacent needle probes are energized and act in the manner of bipolar cautery probes which ablate the nerve and any other tissue between the needle probes. Preferably, the needle probes are designed in such a manner that they are held within the body of the ablation device until the device reaches its desired location. The needle probes can then be extended to penetrate the wall of the esophagus once the device has been positioned. Preferably, the needle probes are designed so that the electric current flows only at their tips so that the depth of the cautery can be focused to minimize damage to the esophagus. Cosman U.S. Pat. No. 4,565,200, Rydell U.S. Pat. No. 5,007,908, Edwards U.S. Pat. No. 5,370,675 and Edwards U.S. Pat. No. 6,129,726, each of which is incorporated by reference herein, disclose various types of electrode needle probe devices which can be used to deliver RF energy to tissue located within the body. Each of these patents discloses a device in which the needle probes are contained within the device until it has reached its desired location, at which time the needle probes are deployed to contact the tissue to which energy is to be delivered.

In the present invention, the needle probes can irradiate around the complete circumference of the device as shown in FIG. 6 or from only a portion of the device as shown in FIG.

Figure 7:
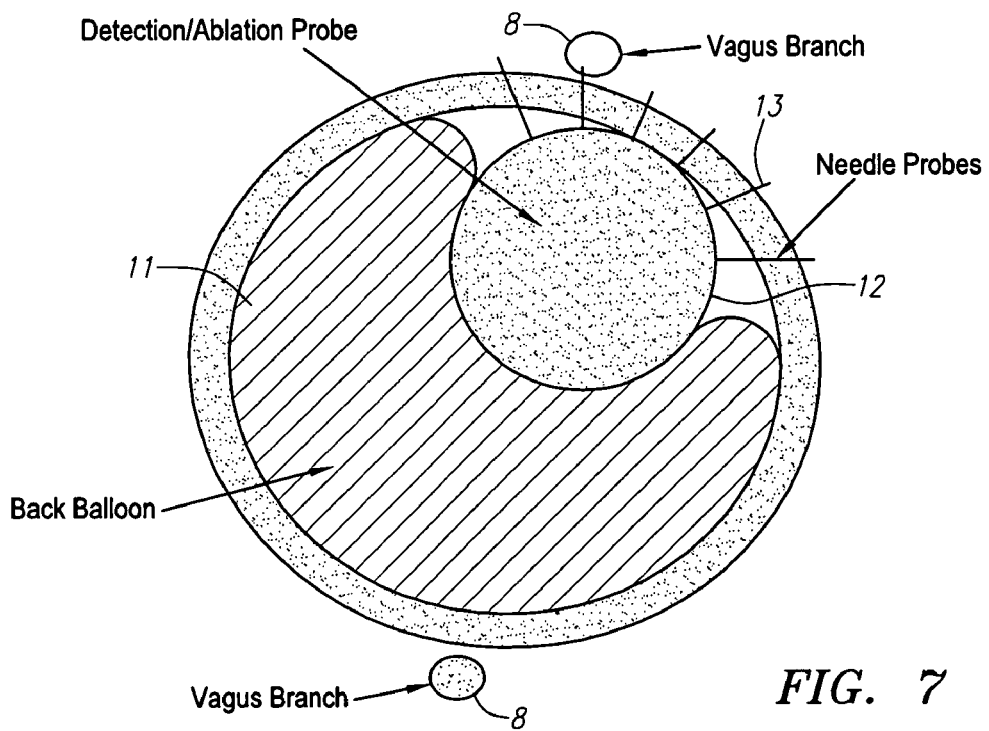
FIG. 7 is an illustration of an ablating device which ablates a sector of the circumference of the outer wall of the esophagus.

7. If the latter, the device can be rotated sequentially to ensure complete coverage. As further shown in FIG. 7, when the needle probes 13 radiate from only a portion of the circumference of the device 12, a back balloon 11 can be used to position the device 12 in the desired location.

Figure 8:
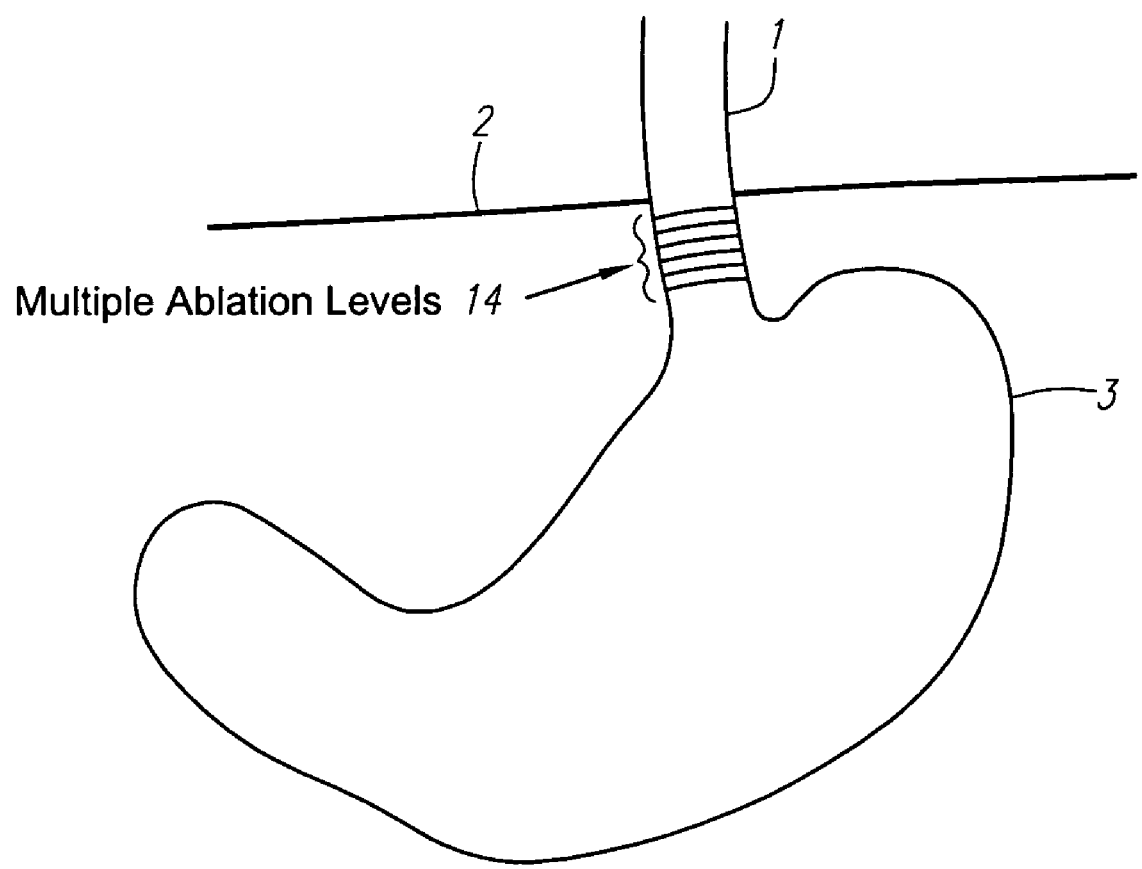
FIG. 8 shows ablating at multiple levels.
Figure 9:
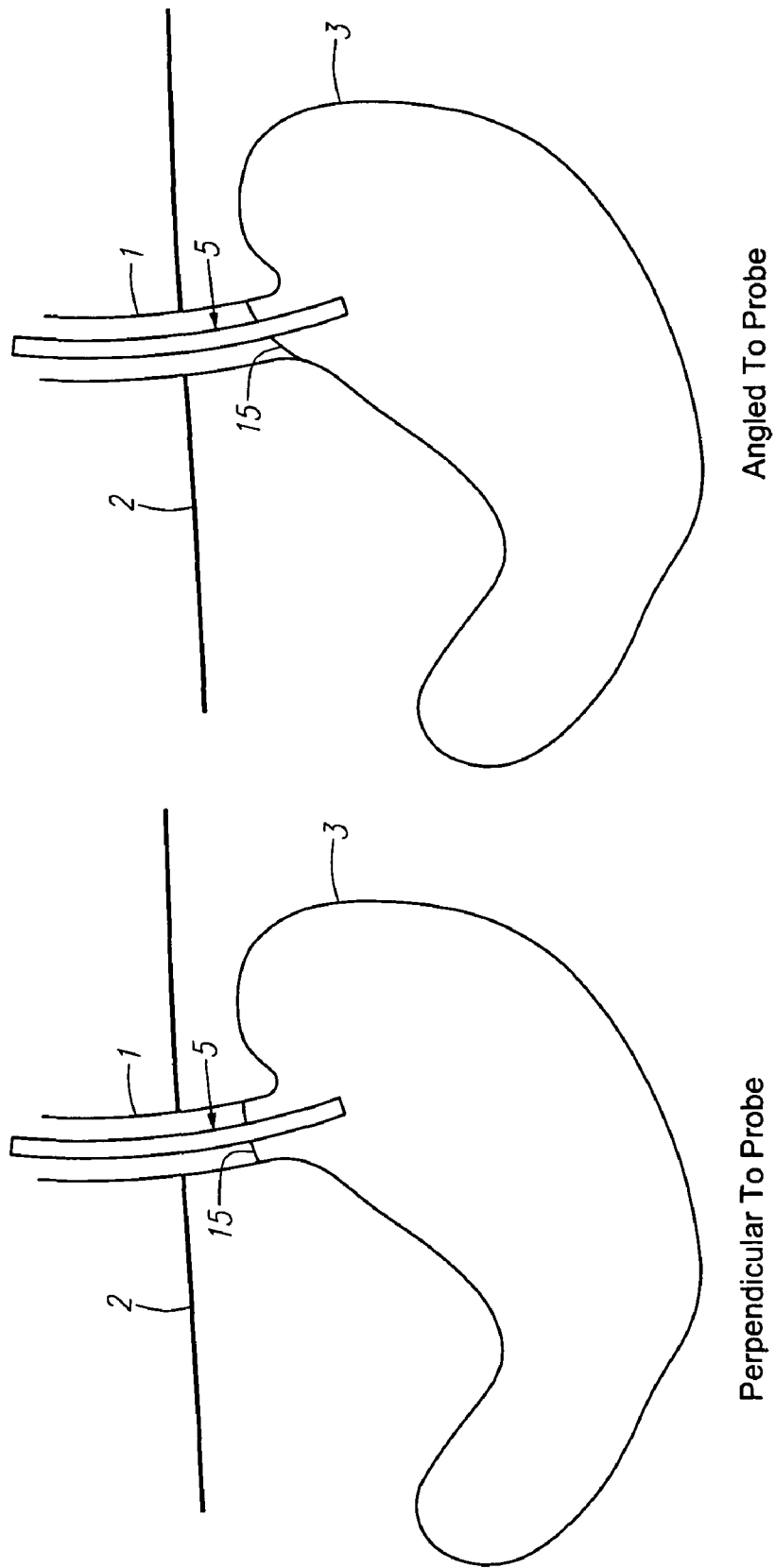
FIG. 9 illustrates an ablation ring which can be adjusted to ablate at different angles relative to the access of the esophagus.
Figure 10:
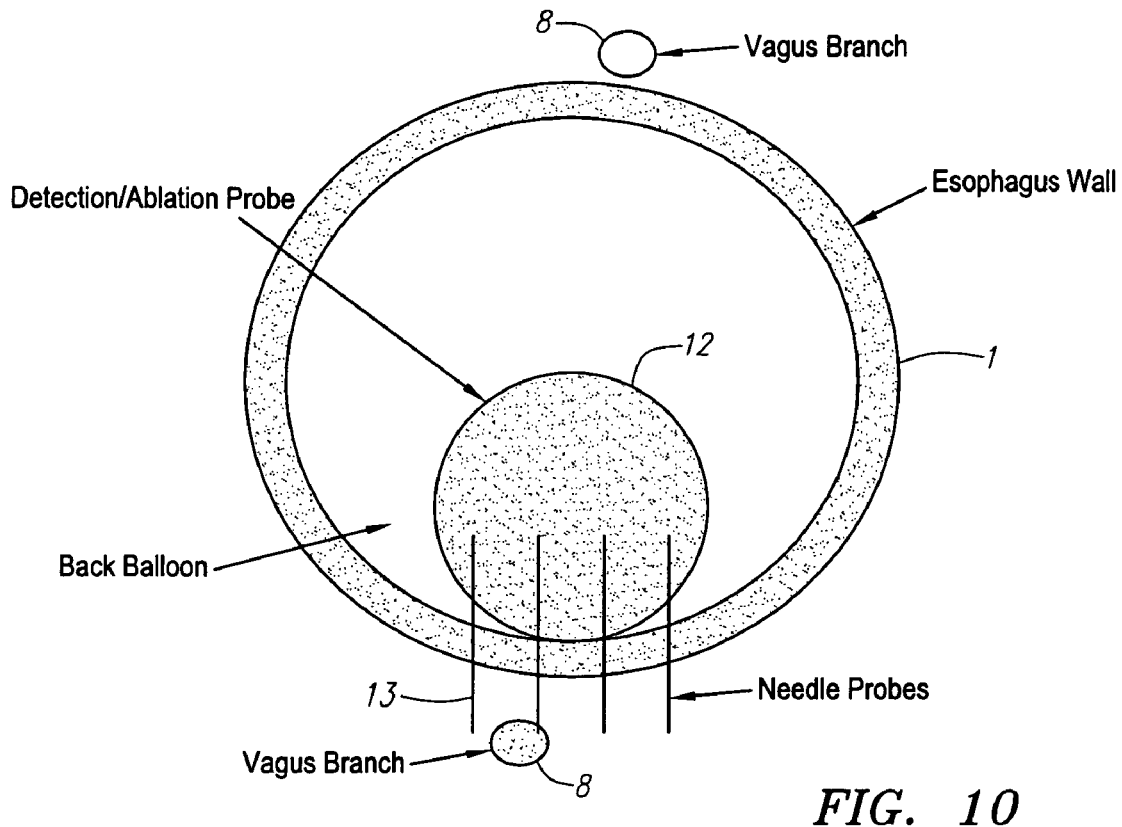
FIG. 10 illustrates the use of still another ablation device to locate and interrupt the vagal nerve.
Figure 11:
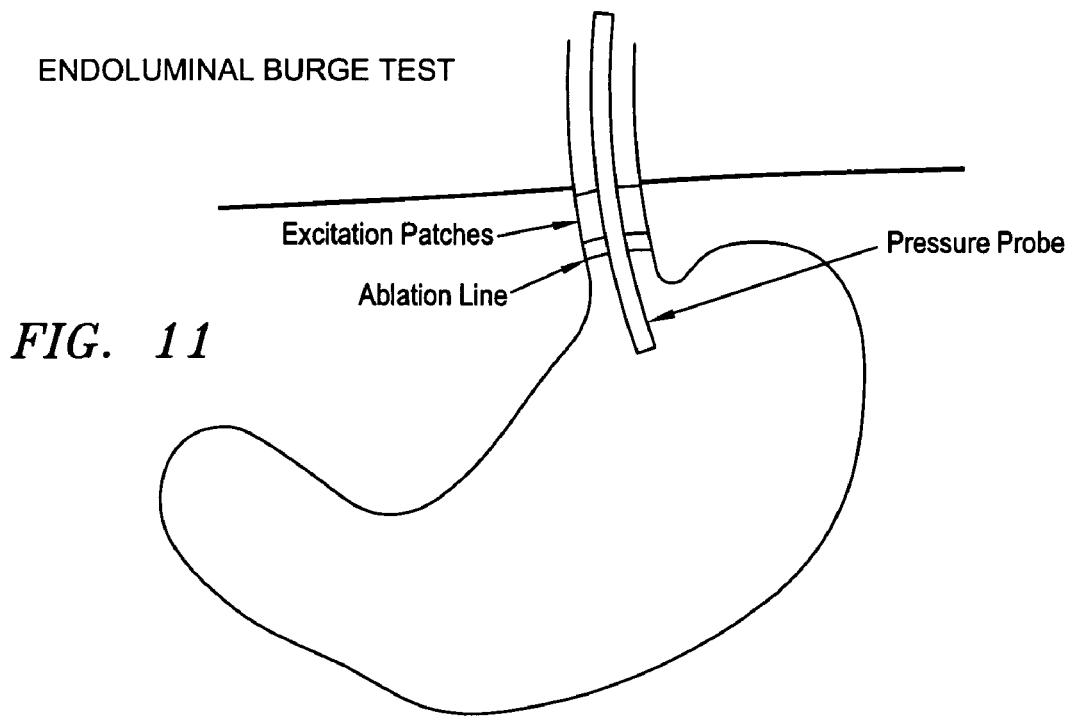
FIG. 11 illustrates an endoluminal burge test which can be used to determine the extent of ablation accomplished.

FIG. 10 illustrates an alternative sector-specific ablation device in which needle probes 13 are activated by device 12 to locate and ablate the vagal nerve in the manner described above. If a patient can obtain the desired benefit of obesity reduction by ablating the two main vagus branches 8, the procedure is simplified and the amount of ablation necessary is reduced. On the other hand, as shown in FIG. 8, if multiple ablation levels 14 are found to be necessary to provide the desired benefit to the patients, more than one ablation can be performed.

If the patient's anatomy makes it desirable, an ablation device 5 can be provided with an energy delivery component 15 which is adjustable such that energy can be delivered perpendicularly to the probe or at an angle to the probe.

When a needle probe is used to deliver energy according to the present invention, the device can be provided with temperature sensors such as thermocouples which are disposed in the distal region of the needle probes. The needle probes can be formed of a variety of materials including nickel-titanium alloy. The needle probes can assume a linear or curved shape when deployed. The device may also be provided with means for cooling the treatment site with a suitable fluid such as water, air, or other liquid or gas, to control the temperature at the treatment site. Thus, the temperature sensor can either cause a cooling medium to be provided or shut off the delivery of energy through one or more needle probes.

In a preferred embodiment of the present invention, high intensity focused ultrasound (HIFU) is used to ablate the vagal nerve branches. The HIFU energy can be transmitted transesophageally to ablate the vagal nerves on the outer wall of the esophagus.

Figure 12:
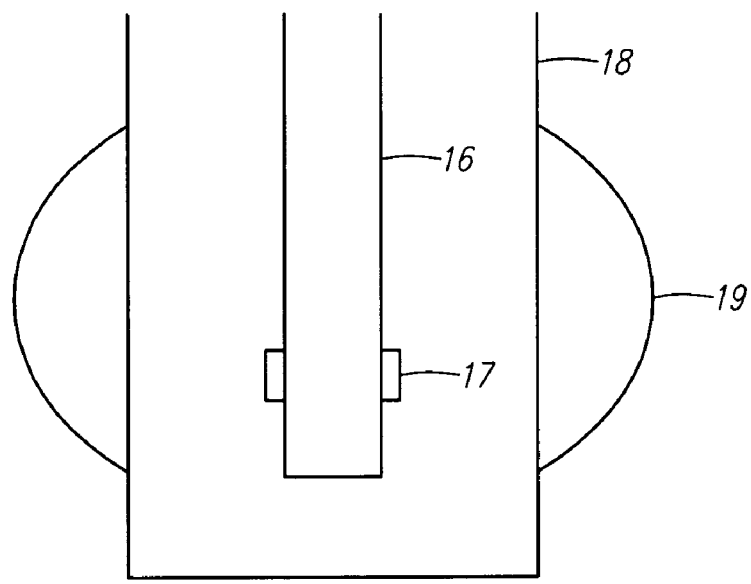
FIG. 12 shows an ultrasound ablating device which may be used according to the present invention.

FIG. 12 illustrates in a diagrammatic form an ultrasound device which can be used according to the present invention. As shown, the device comprises an elongated member 16 which has an ultrasound transducer 17 mounted on its distal region. The elongated member is positioned in a housing 18 which is provided with an inflatable balloon 19. This device may be installed by passing it through the throat and down the esophagus until it reaches its desired location with the balloon 19 deflated. Xray, magnetic resonance imaging, or other known imaging techniques may be used to ascertain the positioning of the treatment device 50, or any other device described herein, in the gastroesophageal region, including axially down the esophagus and rotationally toward the anterior vagus nerve trunk. After rotating the treatment device 50, for example by 180 degrees to target the posterior vagus nerve trunk, the new position of the device 50 may be confirmed by xray, magnetic resonance imaging, or other known imaging techniques. The balloon 19 can then be inflated to position the device and the ultrasound transducer can be activated to transmit energy radially outwardly. Alternatively, a vacuum device can be used to position the housing.

Figure 17A:
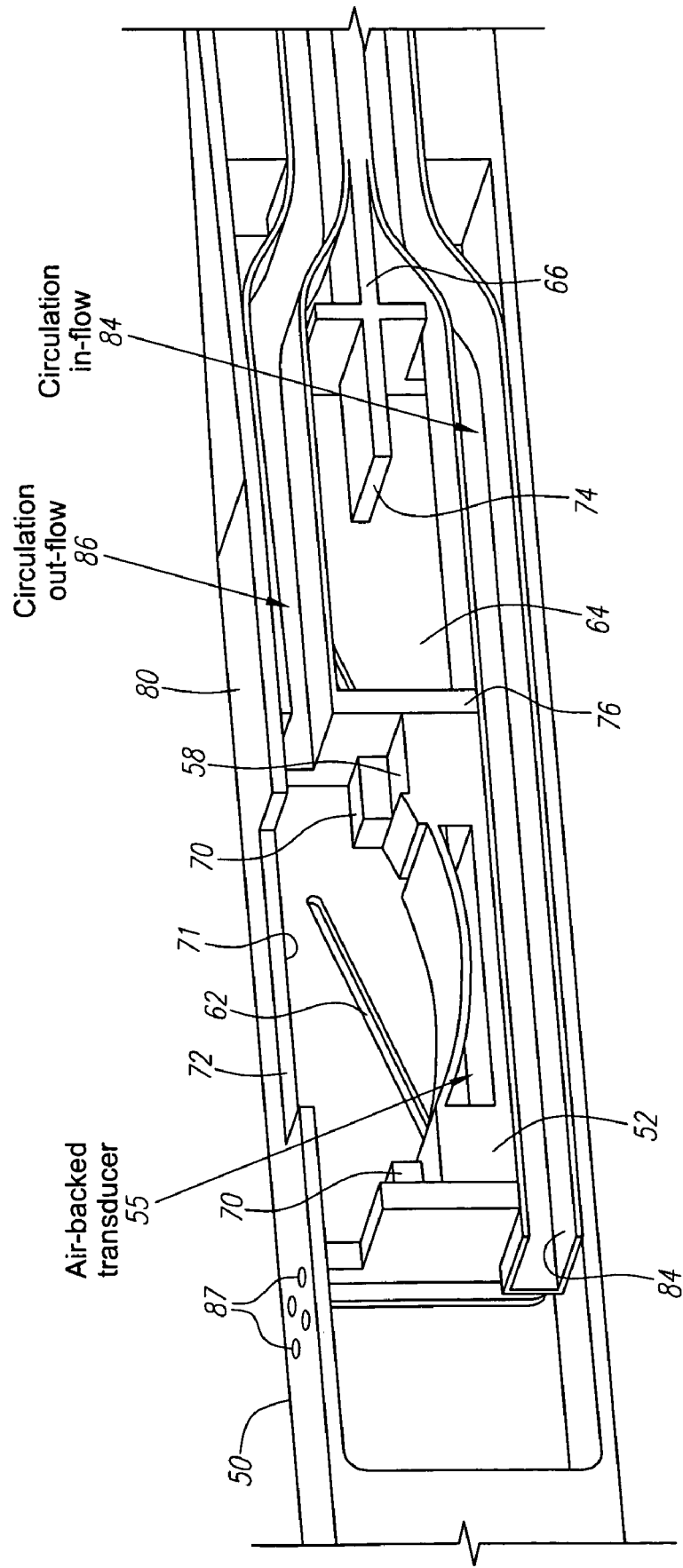
FIG. 17A illustrates a perspective view of a preferred embodiment of the present invention when the ultrasound transducer platform is in a fully lowered position.
Figure 17B:
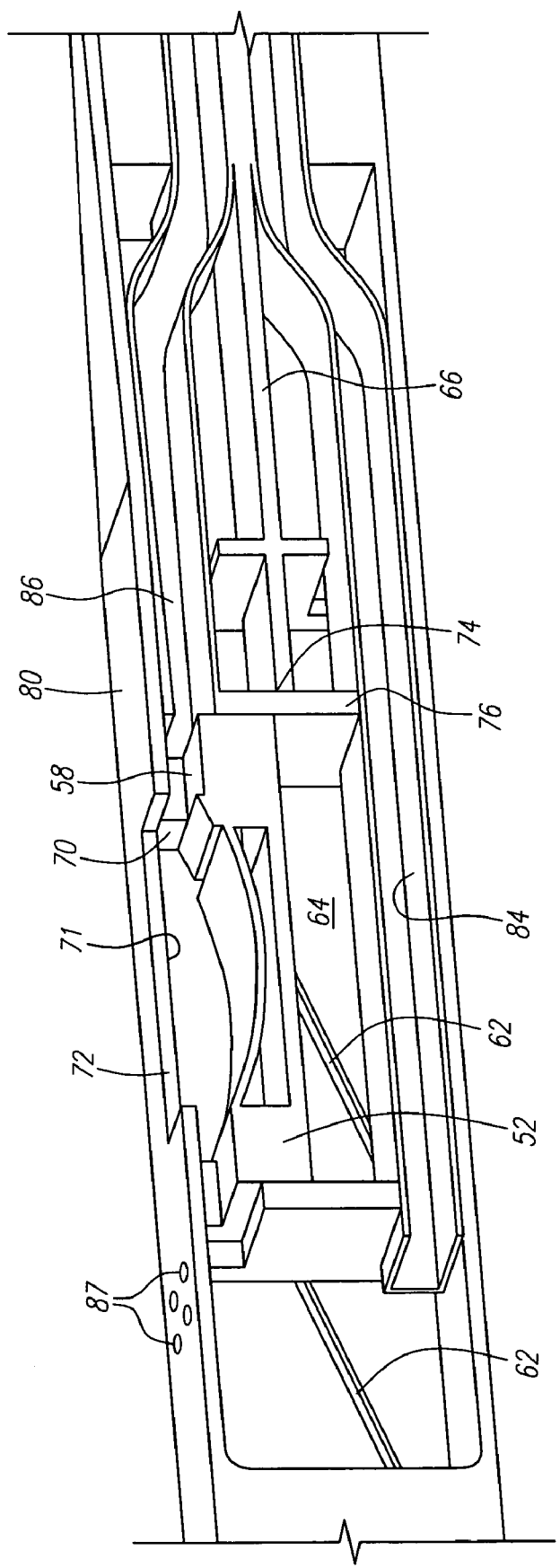
FIG. 17B illustrates a perspective view of a preferred embodiment of the present invention when the ultrasound transducer platform is in a fully raised position.
Figure 20:
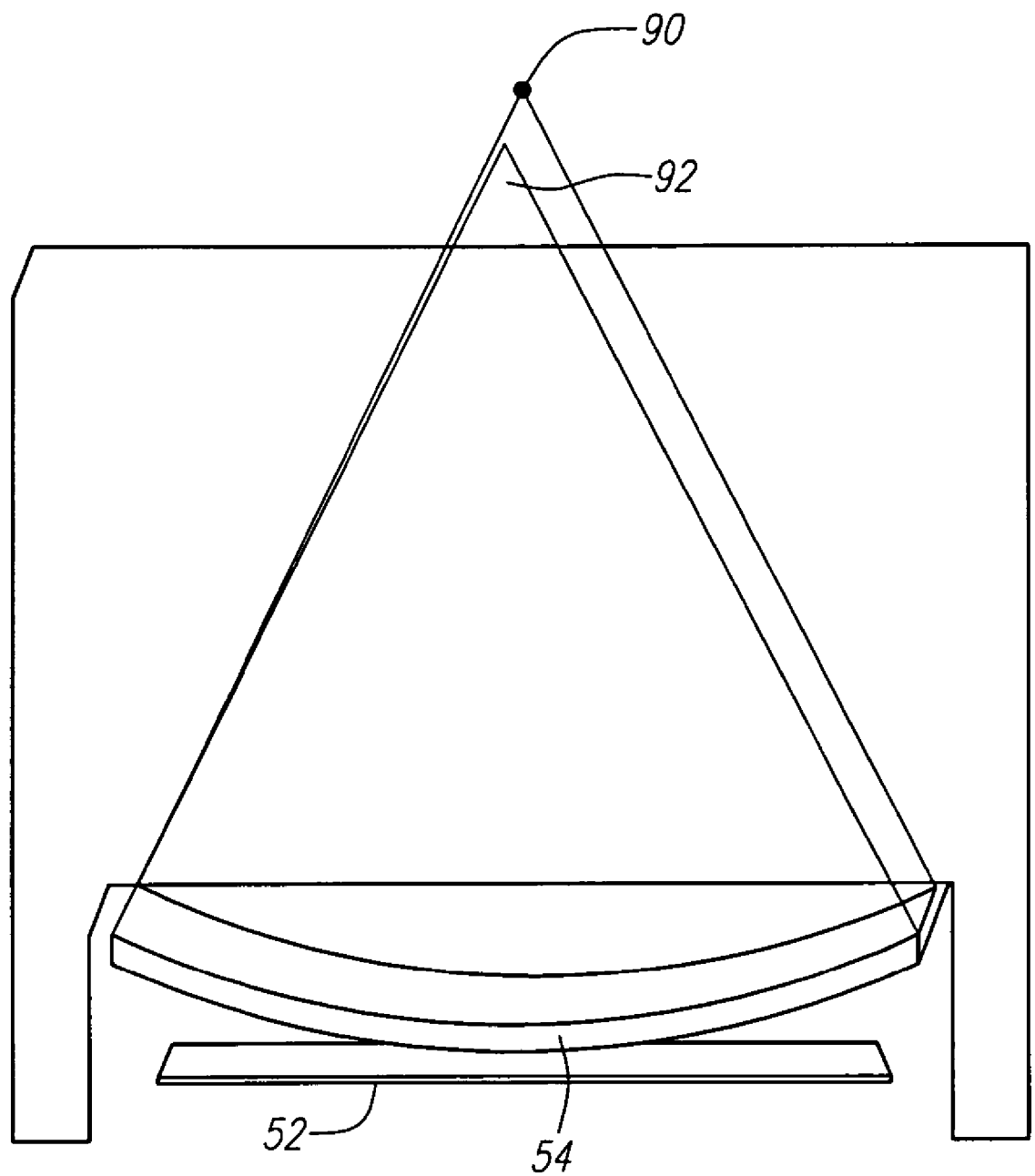
FIG. 20 illustrates an example of the focal point and distribution of energy emitted from the ultrasound transducer.

As shown in FIGS. 17A and 17B, the preferred embodiment of the present invention uses an ultrasound device 54 in a treatment device 50 that is movable along two axes. The treatment device 50 preferably treats obesity by disrupting the gastric vagal nerve adjacent the esophagus. In this example embodiment, a movable platform 52 carries a high focus ultrasound (HIFU) transducer device 54. The transducer 54 may be have an air-backing 55, or other types of known transducer backing materials. FIG. 17A illustrates a perspective view of the preferred embodiment when the platform 52 is in a fully lowered position, while FIG. 17B illustrates a perspective view when the platform 52 is in a fully raised position. Of course, the ultrasound transducer 54 may move anywhere between the fully raised position and the fully lowered position. Thus, the platform 52 may move the ultrasound transducer 54 closer to or farther from a treatment window 72 so as to control the focal point of the energy output from the ultrasound transducer 54. As the ultrasound transducer 54 moves farther from the treatment window 72, the focal point of the energy from the ultrasound transducer 54 moves closer to the wall of the esophagus. FIG. 20 illustrates an example of the focal point 90 and distribution 92 of energy emitted from the ultrasound transducer. Thus, the focal point 90 is adjustable. Preferably, the focal point 90 is directed at the site of a vagal nerve and away from the esophagus wall.

Figure 18:
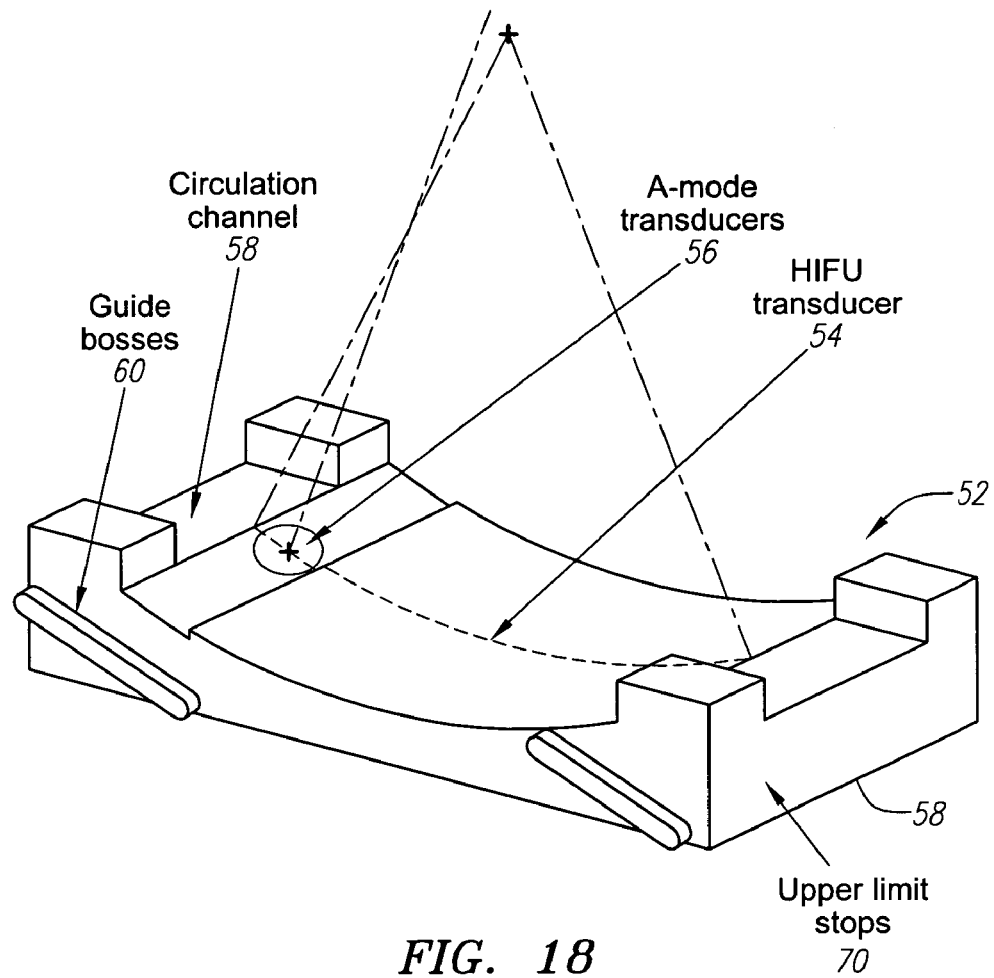
FIG. 18 illustrates a perspective view of a preferred embodiment of the transducer platform.

FIG. 18 illustrates a perspective view of an example embodiment of the transducer platform 52. The platform 52 preferably carries a high intensity focused ultrasound transducer 54 and an ultrasound imaging transducer 56. The ultrasound imaging transducer 56 performs diagnostic imaging for monitoring the formation of lesions in the esophagus and for defining the outside of the esophagus for the purpose of locating the vagal nerve. The ultrasound imaging transducer 56 can be any known type of imaging transducer such as those that are mechanically based (e.g., rotating and pivoting transducers) or piezo electrically based phased arrays, which have, for example, 128 imaging transducers.

The platform 52 also may include circulation channels 58 for allowing fluid, such as saline, to flow into the device and around the ultrasound transducer 54 so as to improve the acoustic characteristics of the ultrasound transducer 54 or to cool the transducer 54. Even though the transducer 54 is illustrated as having a curved surface, the ultrasound transducer 54 may have any geometry, size, shape and curvature as appropriate.

Figure 19:
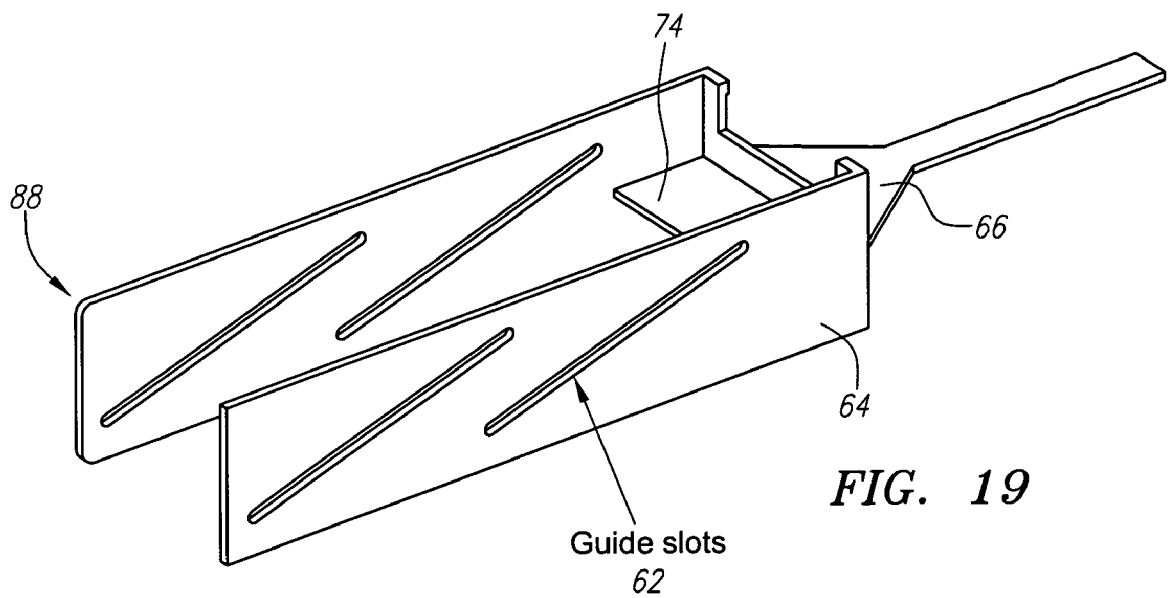
FIG. 19 illustrates a perspective view of a preferred embodiment of a position actuator.

The platform 52 has one or more guide rails or guide bosses 60, which couple to guide slots 62 of the position actuator 64 shown in FIG. 19, which illustrates a perspective view of an example embodiment of the position actuator 64. Because the guide bosses 60 ride in upward slanted guide slots 62, movement of the distal end 88 of the position actuator 64 toward the platform 52 causes the platform 52 to rise toward the treatment window 72. The upper limit stops 70 on the platform 52 create an upper limit of motion for the platform 52. Of course, variations are also contemplated. For example, the guide slots 62 can be in a falling configuration so that movement of the distal end 88 of the position actuator 64 toward the platform 52 causes the platform 52 to retreat from the treatment window 72. As another example, guide bosses 60 and guide slots 62 may be replaced by any other known mechanism, such as gears, levers or a set of guide rails, to translate the platform 52 toward and away from the treatment window. The guide bosses 60 may be on two or more sides of the platform 52, which would require guide slots 62 on two or more corresponding sides of the position actuator 64. The upper limit stops 70 could hang from the inner surface of the wall having the treatment window 72 instead of being on the platform 52.

As shown in FIG. 19, the position actuator 64 has an elongate member 66 so the physician can push the actuator 64 distally or pull the actuator 64 proximally. A forward stop 74 defines the furthest distal position that the position actuator 64 may be moved.

Turning to FIG. 17A, the platform 52 is shown in its fully lowered position. As such, the forward stop 74 of the position actuator 64 is not engaged with corresponding stop 76 in treatment device 50. FIG. 17A also illustrates a nerve mapping device 80, which is preferably a 10×10 constant current impedance grid for nerve mapping. A thermocouple 71 to monitor the mucosal layer may also be provided on the outer surface of the treatment device 50.

An inflow channel 84 and outflow channel 86 may be provided so that fluids, such as saline, may flow through the treatment device 50. Additionally, optional micro holes 87 may be provided in the wall of the treatment device 50 to facilitate the flow of fluids into and out of the device 50.

Comparing FIG. 17A to FIG. 17B, one will see that the position actuator 64 in FIG. 17B is fully inserted so that the forward stop 74 has engaged corresponding stop 76, and the platform 52 is fully raised. Therefore, in this example preferred embodiment, moving the position actuator 64 distally relative to the treatment device 50 causes the platform 52 to move toward the treatment window 72. Conversely, in this example preferred embodiment, moving the position actuator 64 proximally relative to the treatment device 50 causes the platform 52 to move away from the treatment window 72. Thus, the treatment device 50 permits the position of the ultrasound transducer 54 relative to the treatment window 72, and thus, the esophageal wall, to be adjusted. The adjustable positioning of the ultrasound transducer 54 along this axial axis permits control over the focusing of the energy emitted from the ultrasound transducer 54 onto the gastric vagal nerve in the region of the esophagus while minimizing damage to or burning of the esophageal wall.

Besides translation along the axial axis, the platform 52 and ultrasound transducer 54 may be moved longitudinally along another axis to a further or closer distal position. Because the ultrasound transducer 54 can be moved longitudinally, e.g., closer or further from the stomach, the treatment device 50 can be more accurately positioned to ablate or otherwise disrupt the vagal nerve. Moreover, the treatment device 50 may be used to deliver ablating energy to one vagal nerve branch in a transesophageal manner, and then moved to another vagal nerve branch for further disruption of the vagal nerve system or for testing the completeness of the prior disruption of the vagal nerve.

A preferred method of disrupting the vagal nerves is as follows: First, a treatment device 50, or any other device described herein, is positioned at the appropriate location in the esophagus, preferably with the assistance of xray, magnetic resonance imaging, or other known imaging techniques. Such imaging techniques may be used to properly position the treatment device axially down the esophagus and rotationally toward the anterior vagus nerve trunk. Then the inner esophagus is cooled and the ablation depth is adjusted with an imaging crystal along a radial line of the esophagus. High level energy is emitted from the treatment device, such as from a HIFU transducer, to ablate and disrupt the anterior vagal nerve branch. Then the treatment device is rotated by 180 degrees to target the posterior vagus nerve trunk, where the new position of the treatment device may be confirmed by xray, magnetic resonance imaging, or other known imaging techniques. Once the new position of the treatment device is confirmed as being appropriate, the ablation depth is adjusted with an imaging crystal along a radial line of the esophagus and high level energy is emitted from the treatment device to ablate and disrupt the posterior vagal nerve branch.

Figure 13A:
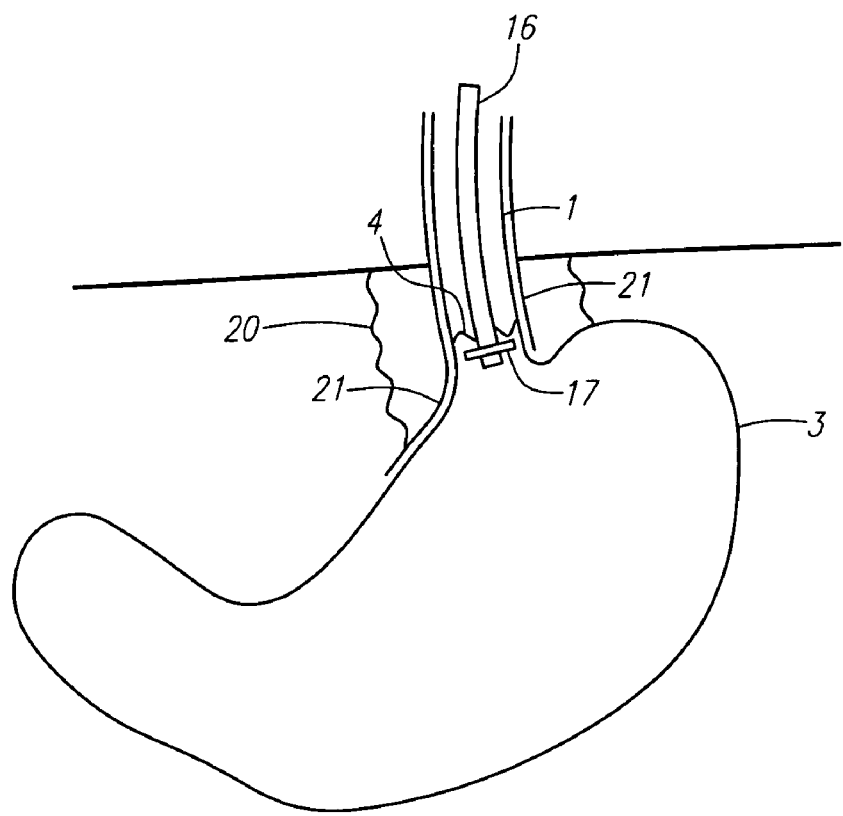
FIG. 13A illustrates an ultrasound device installed in the esophagus.

FIG. 13A is a diagrammatic illustration of an ultrasound transducer installed in the esophagus. As shown in this figure, the transducer device 16 is installed in the esophagus 1 in the region of the Z-line 4. The subhiatal fat ring 20 is also shown. When the transducer 17 is activated, ablating energy will be radiated through the wall of the esophagus to ablate the vagal nerve branches 21 which are also shown diagrammatically.

Figure 13B:
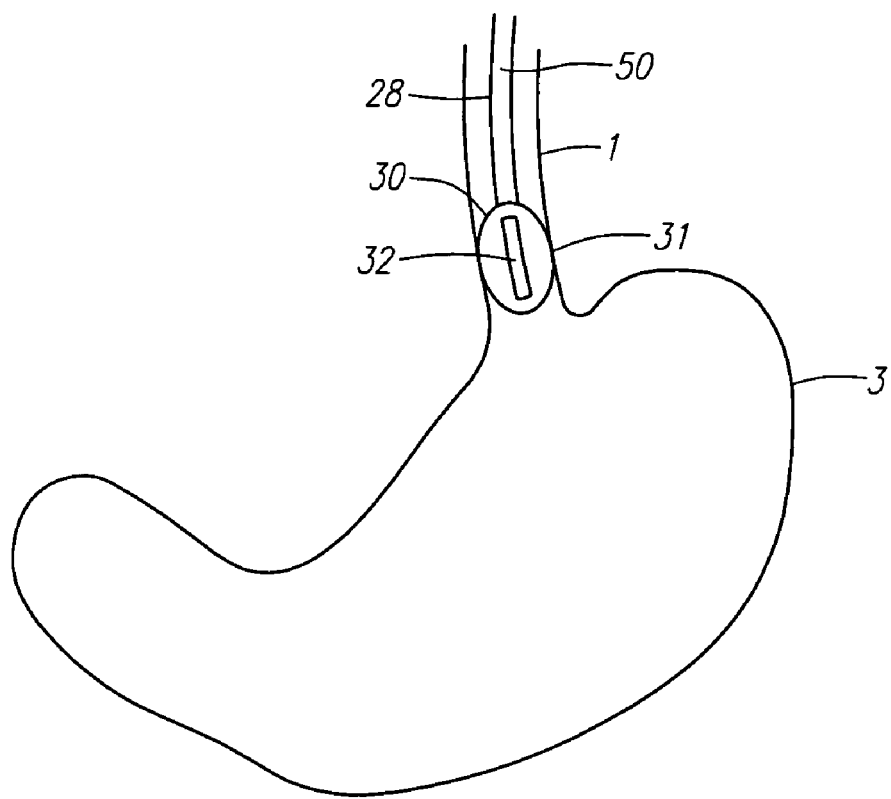
FIG. 13B illustrates the stomach and esophagus with an elongate device with a D-shaped distal tip.
Figure 13C:
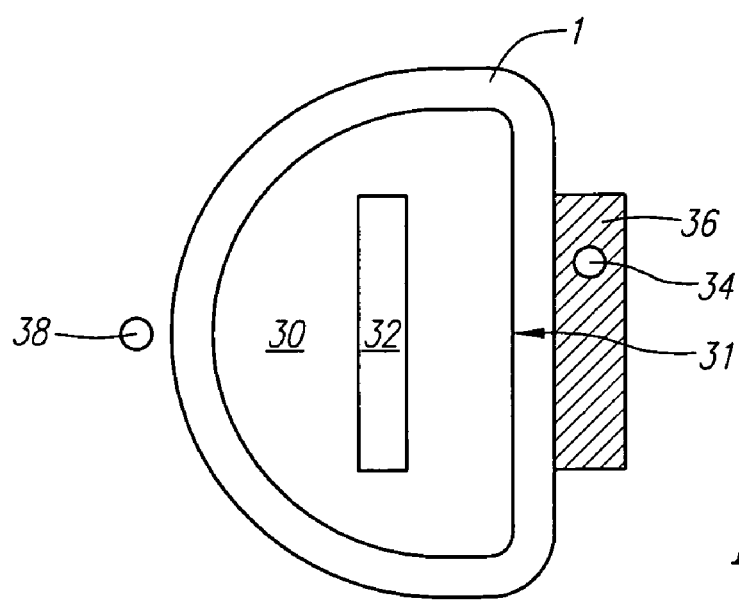
FIG. 13C illustrates a cross section of the esophagus of FIG. 13B to show the D shaped distal tip inside the esophagus.

Although the esophagus is generally illustrated anatomically as a generally cylindrical tube, in its relaxed condition it assumes a more elliptical configuration which can be characterized as floppy. In other words, somewhat like a sock before it is put upon a foot, it does not assume a generally circular configuration unless it contains food or other object, but otherwise has a configuration in which the opposing walls of the esophagus are closer together than they would be when in a circular configuration. For example, FIG. 13B illustrates the stomach 3 and esophagus 1 when an elongate device 28 having a D-shaped distal tip 30 is in place in the esophagus 1. The elongate device 28 is preferably thin, flexible and torqueable. The "D" shape of the distal tip 30 causes the esophageal wall to take on a D shape, with a flat portion 31, as further illustrated in the cross section illustration of FIG. 13C. FIG. 13C illustrates a cross section of the esophagus 1 when the D-shaped distal tip 30 is in place. A HIFU transducer 32 is preferably inside the D-shaped distal tip. By positioning the HIFU transducer 32, which is preferably directed to focus its energy at the flat portion 31 of the D, there is an ablation zone 36 that encompasses the anterior vagal nerve 34. By rotating the D-shaped distal tip 30, the ablation zone can include the posterior vagal nerve 38 or a vagal nerve branch. Thus, when the treatment device 50 is inserted into the esophagus, a cross section of the esophagus would preferably be D-shaped, where the focal point of the energy would be directed in the direction of the flat portion of the "D."

Figure 14:
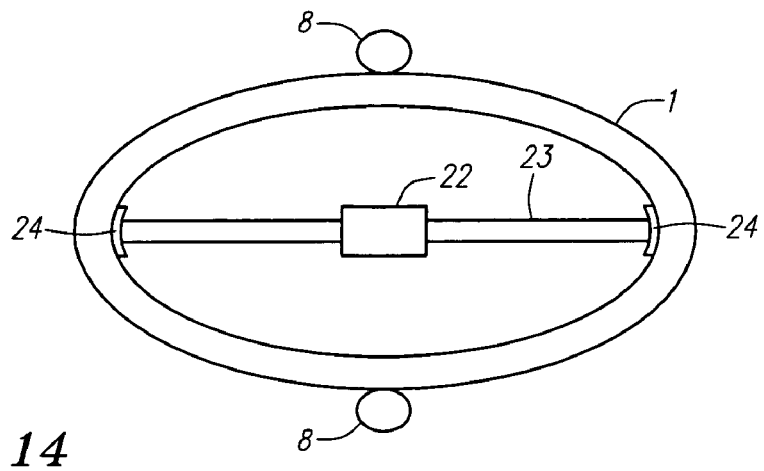
FIG. 14 illustrates an ablation device installed in the esophagus in a manner which shows the esophasgus held in its naturally relaxed configuration by a transducer device.
Figure 15:
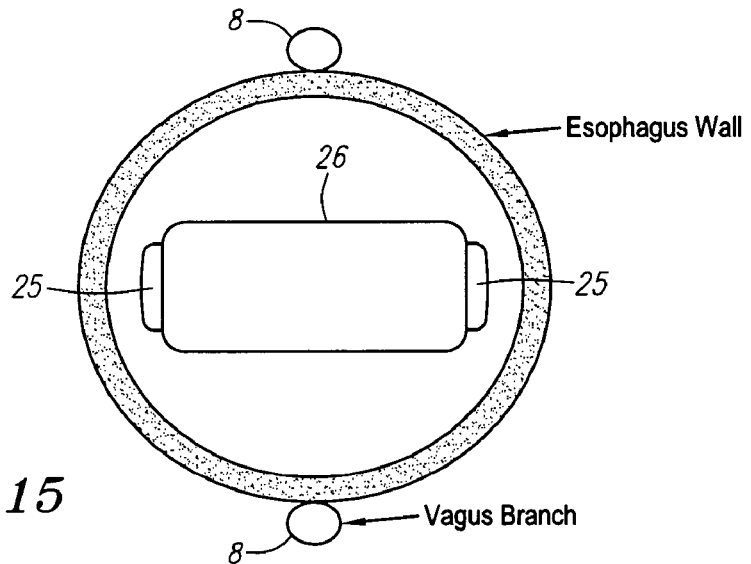
FIGS. 15 and 16 illustrate an alternative to the device shown in FIG. 14.
Figure 16:
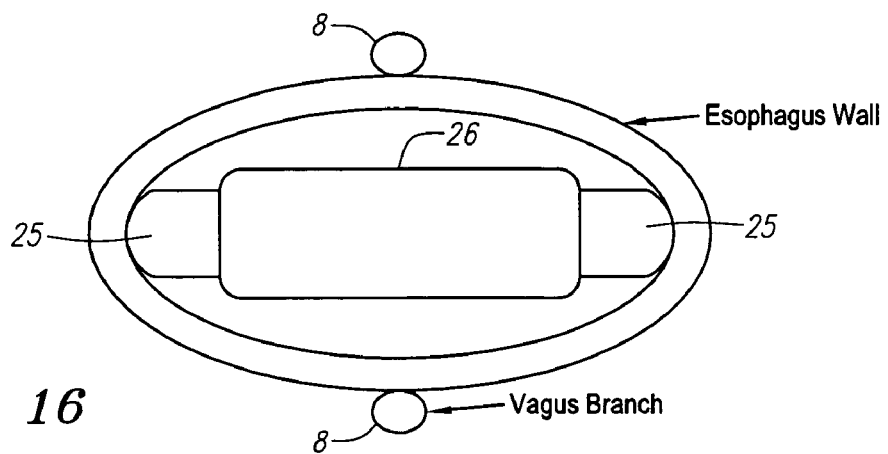

In FIG. 14, esophagus 1 with vagal nerve branches 8 on its outer wall is provided with a transducer 22 which has radially extending struts 23. Each of these struts 23 has a rounded portion 24 at its distal end. The struts 23 and 24 serve to hold the esophagus in its relaxed generally elliptical shape and to hold the transducer 22 in the desired location as well. In an alternative embodiment illustrated in FIGS. 15 and 16, balloons 25 mounted on the side of the transducer-containing device 26 are implemented to hold the esophagus in a more ellipitical shape. When these types of devices are used, the transducer device 22 or 26 could be constructed to direct ultrasound energy towards the vagal nerve branches 8 in one direction or in two directions. FIG. 15 shows the balloons 25 in the deflated state and FIG. 16 shows the balloons in the inflated state.

Ultrasound heating technology, including high-intensity ultrasound and HIFU are well understood. For example, Chapter 12, entitled "Ultrasound heating technology," of "Thermo-radiotherapy and Thermo-chemotherapy," vol. 1, edited by Seegenschmiedt, Fessenden and Vernon, contains a thorough explanation of the use of ultrasound in thermal therapy. This chapter is incorporated by reference herein. In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. As another example, the order of steps of method embodiments may be changed. Features and processes known to those of ordinary skill may similarly be incorporated as desired. Additionally and obviously, features may be added or subtracted as desired. Accordingly, the invention is not to be restricted, but rather to be given the full scope of the attached claims and their equivalents.

We claim:

1. A device for ablating a vagal nerve to disrupt a function of the vagal nerve to reduce obesity comprising:
    an energy delivery device;

a platform adapted to carry the energy delivery device, the platform being adapted to position the energy delivery device along a first axis and a second axis, the first axis being a longitudinal axis of the esophagus and the second axis being a radius of the esophagus, wherein the platform adjusts the position of the energy delivery device along the first axis to control the focus of the energy being delivered to the location of the vagal nerve branch;

a position actuator coupled to the platform, the position actuator moving the platform to adjust the position of the energy delivery device along the first axis, wherein the platform and the position actuator interact through at least one guide rail, and an actuator for energizing the energy delivery device such that energy is delivered to a vagal nerve branch at a level sufficient to ablate the vagal nerve branch.

2. The device of claim 1 wherein the platform moves the energy delivery device along the first axis closer to the vagal nerve branch.

3. The device of claim 1 wherein the platform moves the energy delivery device along the first axis further from the vagal nerve branch.

4. The device of claim 1 wherein the platform is adapted to position the energy delivery device along the second axis to change a location relative to the stomach to which the energy is being delivered.

5. The device of claim 4 wherein the platform moves the energy delivery device along the second axis distally to change the location to another location closer to the stomach.

6. The device of claim 4 wherein the platform moves the energy delivery device along the second axis proximally to change the location to another location farther from the stomach.

7. The device of claim 1 further comprising a slot corresponding to the guide rail.

8. The device of claim 7 further comprising a treatment window adapted to pass the energy to the vagal nerve branch.

9. The device of claim 8 further comprising a stop to set a minimum distance between the platform and the treatment window.

10. The device of claim 1 wherein the guide rail is inclined.

11. The device of claim 1 further comprising a forward stop on the position actuator that limits the forward progress of the position actuator.

12. The device of claim 1 further comprising a diagnostic imaging transducer on the platform.

13. The device of claim 1 further comprising a channel in the platform adapted to circulate a fluid adjacent the energy delivery device.

14. The device of claim 1 further comprising a nerve mapping device.

15. The device of claim 14 wherein the nerve mapping device is a constant current impedance grid.

16. The device of claim 1 wherein the platform is adapted to rotate the energy delivery device about the second axis of the esophagus.

17. The device of claim 1 wherein the energy delivery device is an ultrasound transducer.

18. The device of claim 17 wherein the transducer is a high intensity ultrasound transducer.

19. The device of claim 17 wherein the transducer is a high intensity focused ultrasound transducer.

20. The device of claim 1 wherein the energy delivery device is a radio frequency electrode.

21. The device of claim 1 further comprising a positioning member.

22. The device of claim 21 wherein the positioning member is a balloon.

23. The device of claim 21 wherein the positioning member is a vacuum device.

24. A device for disrupting a function of a vagal nerve comprising:

an energy delivery device;

a platform adapted to carry the energy delivery device, the platform being adapted to position the energy delivery device along a first axis and a second axis, the first axis being a longitudinal axis of the esophagus and the second axis being a radius of the esophagus, wherein the platform adjusts the position of the energy delivery device along the first axis to control the focus of the energy being delivered to the location of the vagal nerve branch;

a position actuator coupled to the platform, the position actuator moving the platform to adjust the position of the energy delivery device along the first axis; and an actuator for energizing the energy delivery device such that energy is delivered to a vagal nerve branch, wherein the platform and the position actuator interact through at least one guide rail.

25. The device of claim 24 further comprising a slot corresponding to the guide rail.

26. The device of claim 25 further comprising a treatment window adapted to pass the energy to the vagal nerve branch.

27. The device of claim 26 further comprising a stop to set a minimum distance between the platform and the treatment window.

28. The device of claim 24 wherein the guide rail is inclined.

* * * * *